(12) United States Patent
Macknik et al.

(10) Patent No.: US 11,350,921 B2
(45) Date of Patent: Jun. 7, 2022

(54) PRESSURE-REGULATING IMPLANT AND METHODS OF USE THEREOF

(71) Applicant: THE RESEARCH FOUNDATION FOR THE STATE UNIVERSITY OF NEW YORK, Albany, NY (US)

(72) Inventors: Stephen Macknik, Brooklyn, NY (US); Olivya Caballero, Brooklyn, NY (US); Manuel Ledo, Brooklyn, NY (US); Susana Martinez-Conde, Brooklyn, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 16/615,968

(22) PCT Filed: Apr. 1, 2019

(86) PCT No.: PCT/US2019/025104
§ 371 (c)(1),
(2) Date: Nov. 22, 2019

(87) PCT Pub. No.: WO2019/191749
PCT Pub. Date: Oct. 3, 2019

(65) Prior Publication Data
US 2020/0093474 A1   Mar. 26, 2020

Related U.S. Application Data

(60) Provisional application No. 62/651,147, filed on Mar. 31, 2018.

(51) Int. Cl.
*A61B 17/02* (2006.01)
(52) U.S. Cl.
CPC ............................. *A61B 17/0218* (2013.01)

(58) Field of Classification Search
CPC .......... A61B 17/0218; A61B 2090/103; A61B 5/6814; A61B 17/02; A61B 2017/0212; A61B 2017/0225; A61F 2/2875
(Continued)

(56) References Cited

U.S. PATENT DOCUMENTS

| 4,265,252 A | * | 5/1981 | Chubbuck | ............... | A61B 5/031 |
| | | | | | 600/561 |
| 4,673,407 A | * | 6/1987 | Martin | ..................... | A61F 2/38 |
| | | | | | 623/20.33 |

(Continued)

FOREIGN PATENT DOCUMENTS

WO   2017031340 A1   2/2017

OTHER PUBLICATIONS

International Search Report and Written Opinion of the International Searching Authority for International Application No. PCT/US2019/025104 dated Jun. 14, 2019.

*Primary Examiner* — Eduardo C Robert
*Assistant Examiner* — Tara Rose E Carter
(74) *Attorney, Agent, or Firm* — Heslin Rothenberg Farley & Mesiti P.C.

(57) ABSTRACT

Provided is an implant, including a chamber having an interior radius wherein the interior radius has a flange, a cover slip, a cup, a setting member, a securing member, a resistance member, and an opposing member, wherein the cover slip, cup, resisting member, and setting member are attached to one another, the setting member sets on a flange and the securing member secures the setting member to the flange, the resistance member includes a flexibility and a longitudinal axis with a length wherein the flexibility permits modification of the length, and the opposing member sets a minimum length of the longitudinal axis. Also pro- (Continued)

vided is a method of using said implant including affixing the chamber to a skull of a mammal.

26 Claims, 10 Drawing Sheets

(58) Field of Classification Search
USPC ......... 623/17.12, 17.13, 17.19; 600/201–245
See application file for complete search history.

(56) References Cited

U.S. PATENT DOCUMENTS

| | | | | |
|---|---|---|---|---|
| 6,113,553 | A * | 9/2000 | Chubbuck | A61B 5/0031 600/561 |
| 2002/0004661 | A1 * | 1/2002 | Sevrain | A61B 17/8888 606/324 |
| 2005/0216084 | A1 * | 9/2005 | Fleischmann | A61F 2/442 623/17.11 |
| 2007/0038100 | A1 * | 2/2007 | Nita | A61B 8/0808 600/439 |
| 2008/0060442 | A1 * | 3/2008 | Smith | G01L 7/061 73/729.1 |
| 2009/0138090 | A1 * | 5/2009 | Hurlbert | A61F 2/4425 623/17.16 |
| 2009/0185980 | A1 * | 7/2009 | Dong | G02B 21/0076 424/9.2 |
| 2012/0184999 | A1 * | 7/2012 | Khanna | A61B 17/688 606/281 |
| 2013/0158670 | A1 * | 6/2013 | Tigno, Jr. | A61F 2/2875 623/17.19 |
| 2014/0135647 | A1 | 5/2014 | Wolf, II | |
| 2014/0330123 | A1 | 11/2014 | Manwaring et al. | |
| 2015/0224299 | A1 | 8/2015 | Wahlstrand | |
| 2015/0320560 | A1 | 11/2015 | Mulliken et al. | |
| 2016/0066803 | A1 | 3/2016 | Hu et al. | |
| 2016/0296312 | A1 * | 10/2016 | Kuhn | A61F 13/12 |

* cited by examiner

PRESSURE-REGULATING IMPLANT AND METHODS OF USE THEREOF

CROSS REFERENCE TO RELATED APPLICATIONS

This application is a national stage filing under 35 U.S.C. § 371 of International Application No. PCT/US2019/025104, filed on Apr. 1, 2019, published as WO 2019191749 on Oct. 3, 2019, and claims priority from U.S. provisional patent application No. 62/651,147, filed Mar. 31, 2018. The entire disclosures of each of the said applications are incorporated by reference in their entireties herein.

GOVERNMENT RIGHTS STATEMENT

The present application was made with support from the National Science Foundation Grant No. 1734887. The government has certain rights in this invention.

FIELD OF THE INVENTION

The subject matter disclosed herein relates to indwelling implants and methods of use thereof. More particularly, this disclosure relates to indwelling implants that permit access to a body cavity of a mammal, such as a cranial cavity or other cavity, such as to permit visual, video, or microscopic inspection within the cavity. An implant as disclosed herein may permit such inspection over a period of days, weeks, months, or longer.

BACKGROUND OF THE INVENTION

Several problems challenge mesoscopic imaging in the brain: 1) difficulty with positioning high-numerical aperture objectives near the brain; 2) creating a flat imaging window against the surface of the brain; 3) adjusting the imaging window to changes in swelling and pressure in the brain, such as those that may occur due to hydration changes and other physiological factors; 4) preventing growth of dura and biofilms that cloud the imaging window; 5) follow-on MRI imaging of the animal post-implantation. Improvements to address these shortcoming are therefore desirable.

The present disclosure is directed to overcoming deficiencies in the art.

SUMMARY OF THE INVENTION

Provided is an implant, including a chamber having an interior radius wherein the interior radius has a flange, a cover slip, a cup, a setting member, a securing member, a resistance member, and an opposing member, wherein the cover slip, cup, resisting member, and setting member are attached to one another, the setting member sets on a flange and the securing member secures the setting member to the flange, the resistance member includes a flexibility and a longitudinal axis with a length wherein the flexibility permits modification of the length, and the opposing member sets a minimum length of the longitudinal axis.

In an embodiment, the resistance member comprises a hydrogel, one or more springs, silicone, or rubber. In another embodiment, the resistance member includes a silicone and the silicone includes a weight ratio of hybrid vinyl-functional siloxane polymer mix (P) to platinum catalyst (C) to silicone-based oil (O) and the weight ratio of P:C:O is 2:10:30. In a further embodiment, a Young's Modulus of the resistance member is between 0.5-1.0 kPa. In still another embodiment, the resistance member includes one or more springs and the implant further includes a protective cover between the one or more springs and the cup.

In yet another embodiment, the implant further includes a cap. In still another embodiment, the opposing member includes one or more screws extending from the setting member and abutting the cup. In an example, the resistance member includes one or more springs, the implant further includes a protective cover between the one or more springs and the cup, and the opposing member includes one or more screws extending from the setting member and abutting the cup or the protective cover.

In still a further embodiment, an outer radius of the setting member includes setting member threads and the inner radius includes chamber threads and the setting member threads mate with the chamber threads. In an embodiment, an outer radius of the setting member includes tabs and the inner radius includes slots and the tabs mate with the slots.

In another aspect, provided is a method of using an implant, wherein the implant includes a chamber having an interior radius wherein the interior radius has a flange, a cover slip, a cup, a setting member, a securing member, a resistance member, and an opposing member, wherein the cover slip, cup, resisting member, and setting member are attached to one another, the setting member sets on a flange and the securing member secures the setting member to the flange, the resistance member includes a flexibility and a longitudinal axis with a length wherein the flexibility permits modification of the length, and the opposing member sets a minimum length of the longitudinal axis, and the method includes affixing the chamber to a skull of a mammal. In an example, the mammal is a primate. In another example, the chamber is affixed to the skull for at least 6 months. In a further example, the chamber is affixed to the skull for at least 12 months.

In another embodiment, provided is an implant, including a setting member, a resistance member, and an opposing member, wherein the resistance member includes a flexibility and a longitudinal axis with a length and the opposing member sets a minimum length of the longitudinal axis. In an embodiment, the resistance member includes a hydrogel, one or more springs, silicone, or rubber. In an example, the resistance member is a hydrogel. In another example, the resistance member is one or more springs. In a further example, the resistance member is silicone.

In another embodiment, the opposing member comprises one or more screws having a head and the one or more screws extend between an inner surface of a bone and an outer surface of the setting member. In an example, the setting member is between one or more head and the bone. In another example, the bone is between one or more head and the setting member.

In another aspect, provided is a method of using an implant, wherein the implant includes a setting member, a resistance member, and an opposing member, wherein the resistance member includes a flexibility and a longitudinal axis with a length and the opposing member sets a minimum length of the longitudinal axis and using includes implanting the implant in a mammal between a brain and a skull of the mammal.

In an example, the mammal is a primate. In another example, the implant is implanted for at least 6 months. In a further example, the implant is implanted for at least 12 months.

BRIEF DESCRIPTION OF THE DRAWINGS

These and other features, aspects, and advantages of the present disclosure will become better understood when the following detailed description is read with reference to the accompanying drawings, wherein.

DETAILED DESCRIPTION OF THE INVENTION

Figure 1:
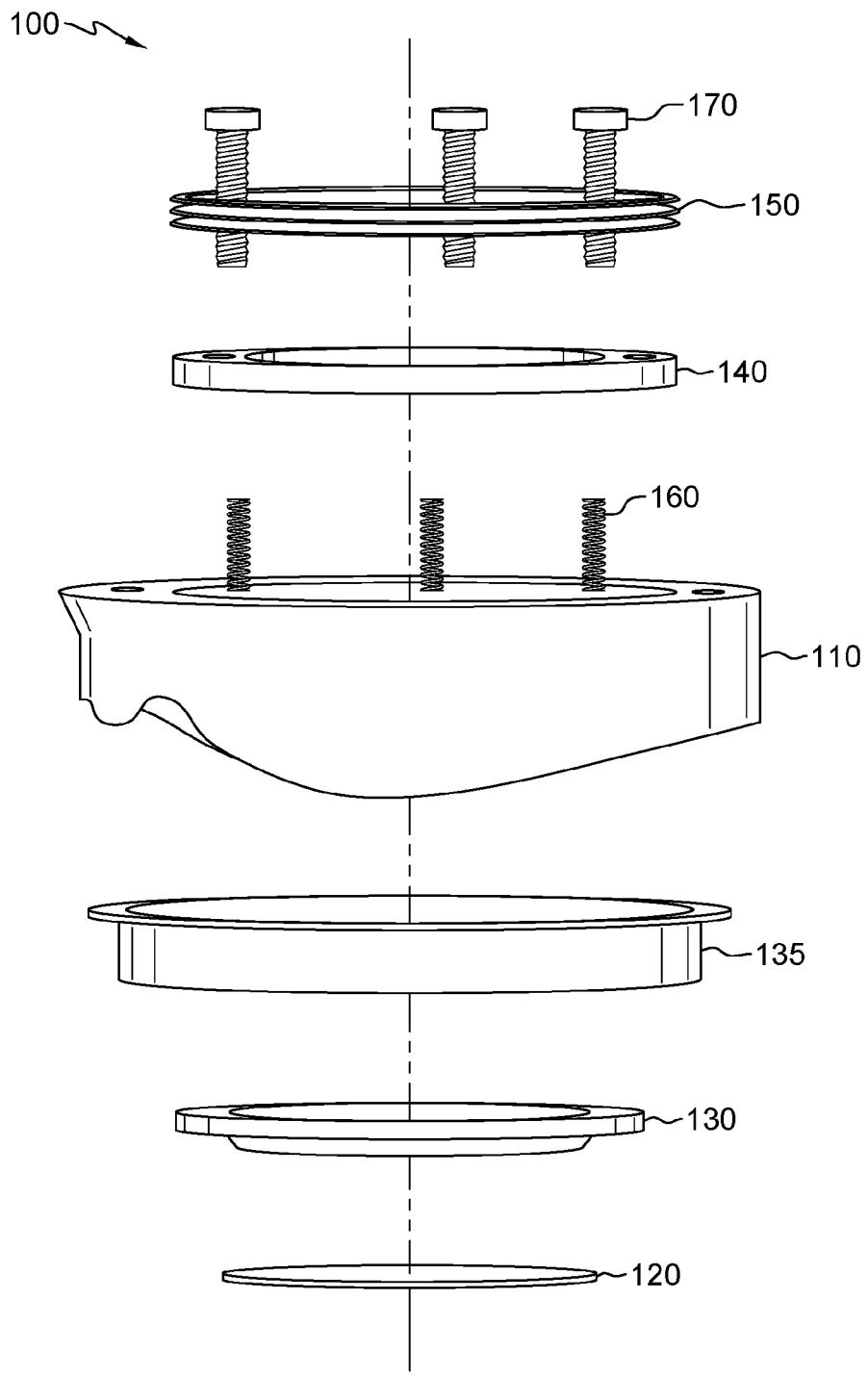
FIG. 1 shows an example of an implant including a protective covering and springs for a resistance member in accordance with aspects of the present disclosure.

Provided is an implant that may be secured to a bone such as a skull to permit long-term observation of tissue within a body cavity such as brain within a cranial cavity. An implant may be implanted on the skull of a primate such as a non-human primate or a human, or other mammal or animal. As disclosed herein, an implant may traverse a bone and include a coverslip through which cells or tissue may be observed such as visually or microscopically or otherwise. Observation of tissue may be desired over a period of months or more, such as for more than 6 months or more than 12 months or for years, particularly where long-term observation of brain tissue is desired. A close apposition of a cover slip to brain surface is desirable to prevent occlusion of observability that may otherwise be cause by infiltration of cells or tissue between the cover slip and the cells or tissue such as neurons intended to be observed. At the same time, given that a brain may move within a cranial cavity, some give, yield, or ability of a coverslip's position relative to the skull to change in response to pressure exerted thereupon by a brain surface is desirable. In accordance with aspects of an implant as disclosed herein, position of a coverslip may yield when normal pressure from a moving brain surface is exerted upon it without causing damage to the brain surface, or minimizing such damage, which may have resulted in the absence of movability of the cover slip in response to pressure exerted thereupon by the brain or other tissue.

Thus, provided is an implant for placing within an opening in, for example, a skull, with a coverslip, and components that maintain a coverslip in close apposition with a surface of the brain or other tissue of interest while permitting some give such that the cover slip may give, retract, yield, or otherwise move in an opposite direction when pressure is exerted thereon by the brain surface. In order to maintain close association between a coverslip and a surface of tissue such as brain surface.

An opening for visualization through a coverslip may be of any size or diameter desired, such as 0.5 cm, 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, 10 cm, or larger, in diameter or size, or any diameter or size therebetween, depending on how visualization is intended or desired to be performed. Openings may be of any suitable size for accommodating microscopic objective lenses, for example, for light, fluorescent, or other microscopy techniques. In an example, a 3 cm diameter window may be maintained by placement of an implant in a skull opening, for use in non-human primates or humans.

Any suitable biocompatible materials for long-term implantation may be included in an implant or parts thereof. In an example, an implant or part thereof may be made of or include polyether ether ketone (PEEK) plastic, a radiolucent, strong, thermoresistant biostable material. Strength of the chamber's attachment to the skull or other bone may be obtained with screws known to be suitable for affixing implants to bone, such as titanium screws or other biocompatible screws or affixers. Screws may affix an implant to bone by being implanted at an angle substantially normal to a surface of bone, or angled such that the threaded ends of screws converge when implanted so as to decrease likelihood of an implant becoming unintentionally or accidentally dislodged, as would be appreciated by skilled persons familiar with arthroscopic implants.

An implant may have several parts including any of various potential features to maintain pressure on an organ within a body cavity such as on the brain. A method uses springs to maintain even pressure of the imaging window on, for example, the brain's surface, despite brain motion, such that pressure exerted on the cover glass by the brain surface causes spring compression, allowing the cover slip to give in response to pressure exerted by the brain rather than exerting back pressure onto the brain and thereby potentially causing tissue damage. Another example includes a hydrogel to achieve the same goal. Other examples include use of a silicone or a rubber or other biocompatible, flexible material that maintains even pressure on a brain surface yet can give and compress to prevent exerting damaging pressure on a brain surface.

Dural growth may be inhibited by blocking migration of migratory biofilm-forming cells between the cover slip and the surface of the brain. For example, an implant as disclosed herein may be configured so as to maintain a distance of 30 µm or less between a cover slip and the surface of the brain to prevent infiltration of cells or other tissue therebetween. Some examples may include a distance between a cover slip and a surface of the brain of 50 µm or less, or 40 µm or less, or 20 µm or less. Thus, sufficient pressure on a cover glass or cover slip may be exerted to maintain close apposition of the cover slip to the brain surface at baseline but permit yielding by the cover slip in response to pressure exerted thereupon by the brain. Additionally, pressure may also be exerted and maintained by the cover slip on the brain surface such that if the brain moves away from the cover slip, or returns to a position after previously exerting pressure on the cover slip by pressing towards it, the cover slip maintains proximity thereto (such as be expansion of the springs, hydrogel, silicone, rubber, or other resistance member).

Also provided is an implant that permits manual positioning or repositioning of a cover slip to create an imaging window for observing a brain or other tissue or organ, which may also accommodates the positioning or repositioning of an electrode penetration slot in the cover slip (for simultaneous imaging and electrode recordings or electrical or other stimulation) or other aperture such as for delivery of substances such as drugs or for sampling of tissue.

For some microscopy methods used to visualize tissue through use of an implant as disclosed herein, it may be advantageous to include a fluid between an objective lens and a cover slip, such as an oil or aqueous solution. In some examples, an implant includes a cup affixed to the cover slip, on the opposite side of the cover slip from the brain, with a fluid-impermeable barrier to permit deposition of such fluid. A cup may then be opposed to a resisting member such as a spring or hydrogel or silicone or rubber or other flexible material configured to maintain a minimal distance between the cover slip and brain surface while minimizing excessive pressure exerted on the brain as disclosed above. A resisting member may be present between a setting member which may be set within and releasably held to a chamber, with the resisting member flexibly exerting pressure between the setting member and the cup and, thus, the cover slip. In another example, the resisting member may directly appose the cover slip rather than a cup. The setting member, resisting member, cup, and cover slip may be affixed to each other so as to be insertable within a chamber and removable from the chamber as a single unit. Cup may be glued to the cover slip with FDA approved dental cement. Together they may create a cup that can hold water or other fluid or material. This may be desirable for water or oil immersion imaging lens microscopy for example.

In some examples, a protective cover may be positioned between the setting member and the cup or between the setting member and the cover slip. The resisting member (springs, hydrogel, silicone, or rubber, or other flexible cushioning as disclosed) may exert pressure between the setting member and the protective cover, between the setting member and the cup, or between the setting member and the cover slip. In some examples, a protective cover may be positioned between a resisting member and a cup so as to avoid disadvantageous exertion of pressure by a resisting member directly on a cup. A protective cover may comprise PEEK or a silicone.

A setting member may be reversibly affixed or affixable within a chamber. A chamber may be a part or piece of an implant directly affixable to a bone such as skull. For example, an opening may be made in the skull and a chamber affixed to the outer surface of the skull around the opening. A bottom of a chamber may be contoured so as to mate with the contours of the outer surface of a skull at the position where the opening is made. For example, a circle of bone may be cut and removed from a portion of skull overlaying a region of the brain observation of which is desired. A chamber may be shaped on one side so as to be contoured so as to sit flush up against the region of bone according to the chamber's footprint surrounding the opening. A chamber may be contoured by any known method for shaping or sculpting or machining material to a pre-determined contour. In some examples, a contoured map or impression may be made of the region of the skull to which the chamber is to be affixed, around an opening in the skull, and used to prepare a computerized three-dimensional model of a mating contour thereof. Such computer model may then be used for producing a chamber according to known methods such as three-dimensional printing.

A chamber may be made of any biocompatible material as any other portion or part of an implant, such as but not limited to PEEK. A chamber may be annular or generally circular but could be of any shape other than rounded or irregularly shaped according to the desired opening size and shape and orientation on a skull. An inner radius (or inner sides lining the inner opening of the chamber above an opening in the skull) of a chamber may have fittings for mating with a setting member. For example, a chamber may have a circular opening and a setting member may be circular. The outer radius of the setting member may be smaller than the inner radius of the chamber such that the setting member may be insertable within the opening of the chamber. The chamber may have a flange or ridge that extends radially inwardly from the inner radius of the chamber which the setting member may be too wide to pass, such that the setting member can be inserted in the opening of the chamber and as far as the flange or ridge but not past the flange or ridge. The flange or ridge may be a circular flange or ridge around the inner radius circumferentially or may be an inwardly oriented tab or tabs or an otherwise discontinuous part of a circumferential flange or ridge or portion or portions thereof.

In another example, a setting member may have a tab or tabs that extend radially outward from its outer circumference. And a chamber may have slots running longitudinally down its inner circumference such that the tabs of the setting member may matingly engage with the slots so as to slide down them as the setting member is inserted into the chamber. Other comparable features and shapes for orienting a setting member within a chamber may also be used in like manner, such as a pin or pins or bump or bumps or other protuberance or protuberances may extend radially outward from an outer circumference of a setting member so as to engage or mate with complementary slits, tracks, or other invaginations in the inner circumference of a chamber (and running longitudinally along and inner circumference of said chamber) for positioning of the setting member upon insertion therein. Alternatively, such tabs or pins or other protuberances may extend radially inward from an inner circumference of a chamber to engagingly mate with corresponding tabs or slots or invaginations in the outer circumference of a setting member.

In some examples, a securing member may reversibly affix a setting member within a chamber. A securing member may function to hold a setting member in place within its position in a chamber so as to prevent its movement such as during observation of tissue through the implant. A securing member may be, for example, a ring or other shape that fits within a chamber's inner circumference. A securing member may be inserted within a chamber atop a setting member and be reversibly affixed or affixable to the chamber so as to secure the setting member in place and hold it in position relative to the chamber. Such affixation may be desirable, for example, when observing tissue through the implant, such as via microscopy. In an example, a securing member is annular and fits within an annular inner circumference of a chamber. A securing member may have threads that meet with threads on an inner circumference of a chamber such that a securing member may be screwed down within a chamber until it meets with the setting member and thereby hold the setting member in place, i.e., prevent movement of the setting member relative to the chamber. In another example, the setting member may have a tab or tabs or pin or pins or other protuberance extending radially outward from its circumference that slidably engage with corresponding slots or tracks or other invaginations in the inner circumference of a chamber (extending longitudinally along a chamber's inner circumference) to permit insertion of a securing member into the chamber. In another example, the slots of the chamber inner radius may have circumferential extensions just above where the setting member sets to permit locking of the tabs of the securing ring therein upon rotation of the securing member when its tabs descend to the circumferential extensions. In a non-limiting example, an opening within a chamber may be circular, and a cup, setting member, securing member, or any combination of two or more of the foregoing, may be generally ring-shaped or annular. In another non-limiting example, a cap, cover slip, or both, may be circular. Other shapes of all of the foregoing are also possible in accordance with aspects of the present disclosure.

A cover slip, cup, protective cover, resistance member, and setting member (or subcombinations of the foregoing in examples where fewer than all of said member are present in an implant) may be affixed together such that insertion of a setting member (to which other said members are affixed) into a chamber also includes inserting said member into a chamber. For example, when observation of tissue such as a brain through a chamber's opening is desirable, a setting member, resistance member, protective cover, cup, and cover slip, optionally attached to each other, may be inserted into the chamber's opening, though the opening in the skull overlaid thereby. The cover slip may thus be apposed to the surface of tissue such as brain. A securing member may then be engaged to hold a setting member in place and thereby hold the resistance member, protective cover, cup, and cover slip in place. A microscope objective or other visualizing tool or instrument may then be inserted towards the cover slip for observation of neural tissue.

An implant may also include a cover that may be placed upon or secured atop a chamber to cover the opening therethrough when observation of tissue through the implant is not occurring. A cover may be made of any biocompatible material suitable for implants, including PEEK. A cap may be affixable to a chamber via threads permitting screwing a cap onto or into a chamber, or a cap may be affixable to a chamber with screws or pins, configures to pass through holes in the cap and into correspondingly positioned holes in the chamber, such as threaded holes for mating with screw threads. In some examples, between the cap and the chamber may be a gasket such as a silicon gasket to promote sealing for prevention of foreign particles or fluids from entering within or exiting or seeping from the implant between sessions during which a cap is removed. A chamber may also have other pins, holes, clamps, or recessions for accepting other pins, screws, clamps, etc., configures to permit attachment of devices thereto, such a aspects of microscopy machines, drug infusion or injection tools, electrophysiological measurement or brain stimulation devices, etc., for holding such instrumentation in consistent position relative to a chamber during usage.

As explained above, a resisting member has a flexibility permitting it to be squeezed or expanded in a direction along a longitudinal axis of an implant (i.e., towards or away from tissue surface such as brain surface), which is itself along a longitudinal axis of the chamber, such that a longitudinal axis of the resisting member may be reduced or expanded, or a distance between a cover slip and setting member may be decreased or increased, respectively. A resisting member may have a Young's modulus configured so as to maintain close apposition of a cover slip with a surface of tissue such as a brain but permit compression of the resisting member along its longitudinal axis in response to pressure exerted on the cover slip by the tissue surface. Brain may have a Young's modulus of only 0.5-1.0 kPa. A resisting member may have an accordingly low Young's modulus of between 0.5-1.0 kPa. an example of an opposing member.

In non-limiting examples of embodiments, a resistance member may be silicone or rubber, or other flexible, biocompatible materials. For example, a resistance member may include fluorosilicone with a platinum cure. Different relative weight ratios of, for example, a hybrid vinyl-functional siloxane polymer mix (P) to platinum catalyst (C) to silicone-based oil (O). Various ratios of these components may create silicone with different Young's modulus and can act as resistance members with differing mechanical properties for resistance members with different uses. In a specific, non-limiting example, a combination of these components at a ratio of 10:2:30 of siloxane polymer:catalyst:oil produced a silicone with a Young's modulus comparable to that of soft tissue. Other ratios of P:C:O are also possible in accordance with aspects of the present disclosure, such as 10:2:20 and 10:1:30. Ranges around these relative values are also possible, giving ranges of permissible ratios. Some non-limiting examples of ranges of ratios of P:C:O include 5-15 siloxane polymer to 0.5-5 platinum catalyst to 20-40 silicone-based oil.

Figure 10:
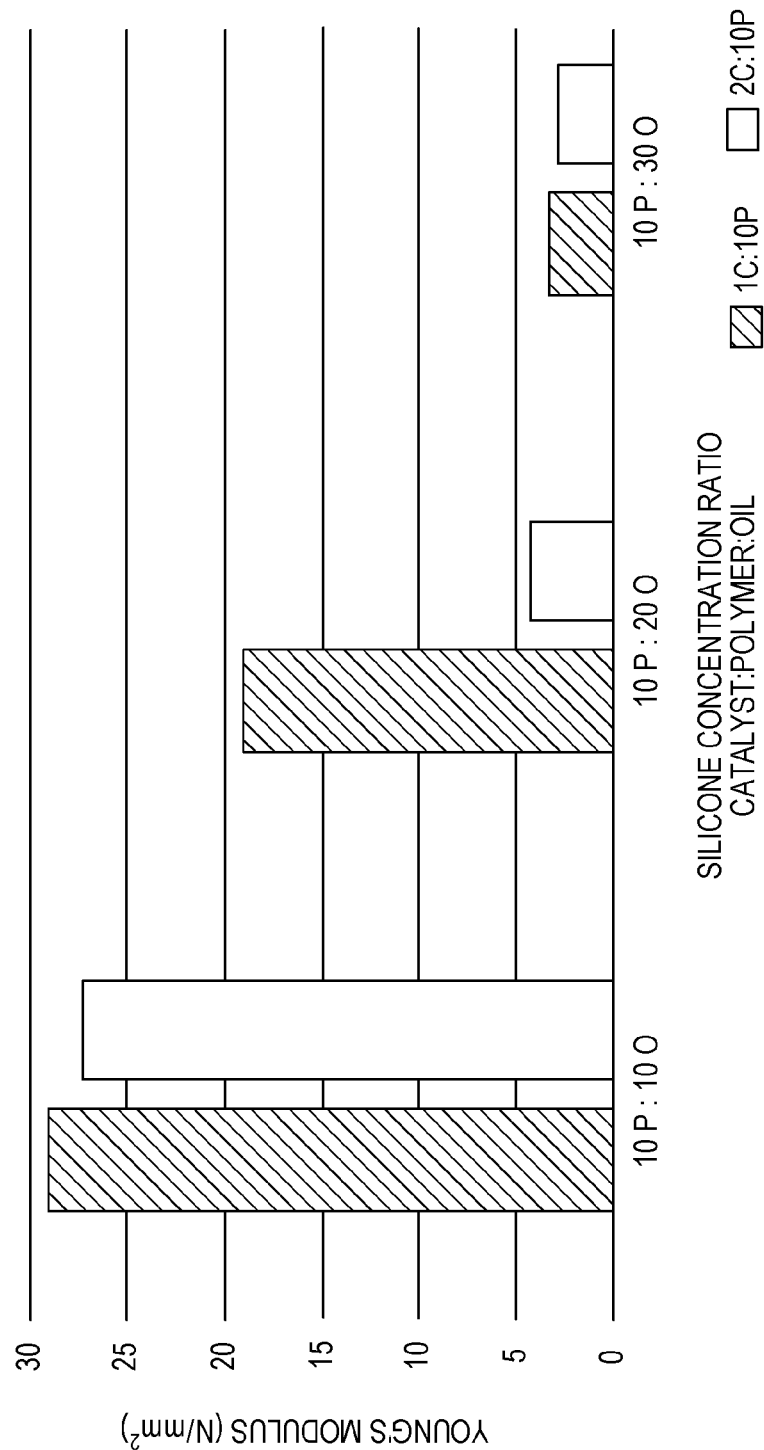
FIG. 10 is a graph depicting different Young's moduluses of different ratios of polymer mix to platinum catalyst to oil.

A resistance member made with such silicone may hydrophobic and inert in biological environments. Shown in FIG. 10 is a graph depicting different Young's moduluses of different ratios of polymer mix to platinum catalyst to oil. In other examples, different materials may be used for a resisting member such as rubber or other compressible or flexible material with a suitable Young's modulus.

Other materials have mechanical properties that can be manipulated to function as resistance members. For example, there are multiple types of hydrogel that can function as a resistance member. A hydrogel that is useful as a non-limiting example of a resistance member is sodium alginate hydrogel. It may be created by combining 0.5% w/v sodium alginate with 1% w/v $CaCl_2$) solution. Said hydrogel is that drugs and other small particles can be mixed in with sodium alginate solution before combining it with $CaCl_2$) solution to embed it in the hydrogel. Said material is hydrophilic and when exposed to an aqueous environment, such added particles or substances may diffuse out of the hydrogel at a constant rate. Implants may be embedded with, for example, antibiotics or other drugs to prevent the risk of infection or foreign body rejection. Still other non-limiting examples of material that may be included in a resisting member include latex, neoprene rubber, Buna-N rubber, and EPDM rubber, as but a few examples.

In some examples, an opposing member may oppose deflection or movement of a cover slip to less than a minimal allowable distance from a setting member. An opposing member may function to maintain a cover slip sufficiently close to the surface of the brain to prevent biofilm formation or formation of other features that may occlude visibility. The opposing member may be adjustable such that a minimum allowable distance between a setting member and a cover slip may be modified. An opposing member may, for example, include one or more screws threaded through threaded holes in a setting member and terminating on a protective cover or cup or cover slip, or at least to prevent such components from moving closer to a setting member than such ends of such, for example, screws, in the event a longitudinal axis of a resisting member otherwise compresses to below a certain length. When an opposing member includes one or more screws with heads extending above, for example, the setting member, the screws may be tightened or loosened to increase or decrease, respectively, a minimum allowable distance between a setting member and a cover slip. An opposing member may instead include other adjustable clamps or slotted rods or pins that can be adjustable moved along a longitudinal axis of an implant to set a minimum permissible distance between a setting member and a cover slip.

A cap may be affixed while a securing member, setting member, resisting member, protective cover, cup, and/or cover slip remain within the implant. Or, any one or more of these components may be removed before affixation of a cap. Removable affixation of a securing member and a setting member allow for exchange of components such as if a portion becomes damaged or worn out over time without requiring removal or replacement of a chamber. Such components may, however, remain within an implant after a cap is affixed and indwell within a subject between sessions during which tissue such as a brain is observed during cap removal.

Referring to a non-limiting example depicted in FIG. 1, an implant 100 may include a chamber 110 contoured to an outer surface of a bone such as a skull such that it may be attachable to the bone. Screws or other affixation components or parts or adhesive, not shown, may secure the chamber to the bone. The chamber has an interior opening. The opening may be circular, or generally circular, or another shape to permit passage of other components therethrough, such as square or rectangular or triangular, etc. A craniotomy may be performed to remove a portion of bone such as a portion of skull permitting access to a body cavity such as a cranial cavity through the inner opening. In some examples the inner opening may be referred to as a radius but as would be understood it need not be circular.

A cover slip 120 (such as made of glass or other material through which imaging may be performed or tissue visually observed, such as a clear or translucent plastic) is affixed to a cup 130. The cup 130 may be affixed to a protective cover 135. The protective cover 135 may be made of silicone or another suitable biocompatible material. The protective cover 135 may be secured to a setting member 140. Also shown is a securing member 150, The setting member 140, protective cover 135, cup 130, and cover slip 120 may be lowered into a chamber 110 as shown in FIG. 1. The inner radius of the chamber may have a flange or other internal protrusion, such as a ridge or radially projecting tabs or other features upon which the setting member may rest without passing further through the chamber. A securing member 150 is shown as a threaded ring in this example though other shapes and orientations may be used in the alternative to this non-limiting example. The securing member 150 may be inserted in the chamber and hold or affix the setting member 140 to the chamber 110 or otherwise hold the position of the setting member 140 along a longitudinal axis of the chamber 110. A securing member 150 may have threads that mate with threads within the chamber's inner radius such that it may be screwed into place and thereby secure the setting member 140 in place, holding it to a flange, ridge, etc., on the inner radius of the opening of the chamber 110. In other examples the securing member 150 may have tabs that engage slots in the inner radius of the chamber 110. In such an example, not shown, slots may run longitudinally along the inner radius of the chamber 110 and tabs may extend outwardly and radially from the securing member 150, such that setting the securing member within the chamber 110 inner radius may include sliding the tabs trough the slots.

A resistance member 160 is shown in this non-limiting example as a plurality of springs. The plurality of springs 160 may be between the securing member 150 and the protective cover 135, or between the setting member 140 and the cup 130, or between the setting member 140 and the cover slip 120. A resistance of the springs 160 permits modification of a distance between the cover slip 120 and the setting member 140; at rest springs 160 maintain a distance therebetween but such distance may be decreased or increased by increasing or decreasing, respectively, pressure exerted on the cover slip 120 towards the setting member 140. That is, the resisting member 160 has a flexibility permitting it to be squeezed or expanded in a direction along a longitudinal axis which is itself along a longitudinal axis of the chamber 110, such that a longitudinal axis of the resisting member 160 may be reduced or expanded, or a distance between a cover slip 120 and setting member 140 may be decreased or increased, respectively.

An opposing member 170, in this non-limiting example, is shown as height-adjusting screws. An opposing member 170 prevents a cover slip 120 from getting less than a minimum allowable distance from the setting member 140. In this example, opposing member 170 height adjusting screws have a head extending above the setting member 140 and a base extending below the setting member 140 and may abut, directly or indirectly, the protective cover 135 or cup 130 or cover slip 120. By abut in this case is meant may be directed towards and could touch, directly or indirectly, the protective cover 135 or cup 130 or cover slip 120, when the minimum allowable distance is attained. The screws 170, being threaded through threaded holes through, for example, the setting member 140, may be held in place once positioned, such that when contacted directly or indirectly by the protective cover 135 or cup 130 or cover slip 120, the cover slip 120 is prevented by the bottoms of the screws 170 from getting less than the minimum allowable distance from the setting member 140. For example, the minimum distance may be determined by a distance from which screw 170 bottoms extend from the bottom of threaded screw holes in the setting member 140. Screws 170 may have flat bottoms or shaped bottoms for fitting within specific features or notches of a protective cover 135 or cup 130 or cover slip 120.

Figure 2:
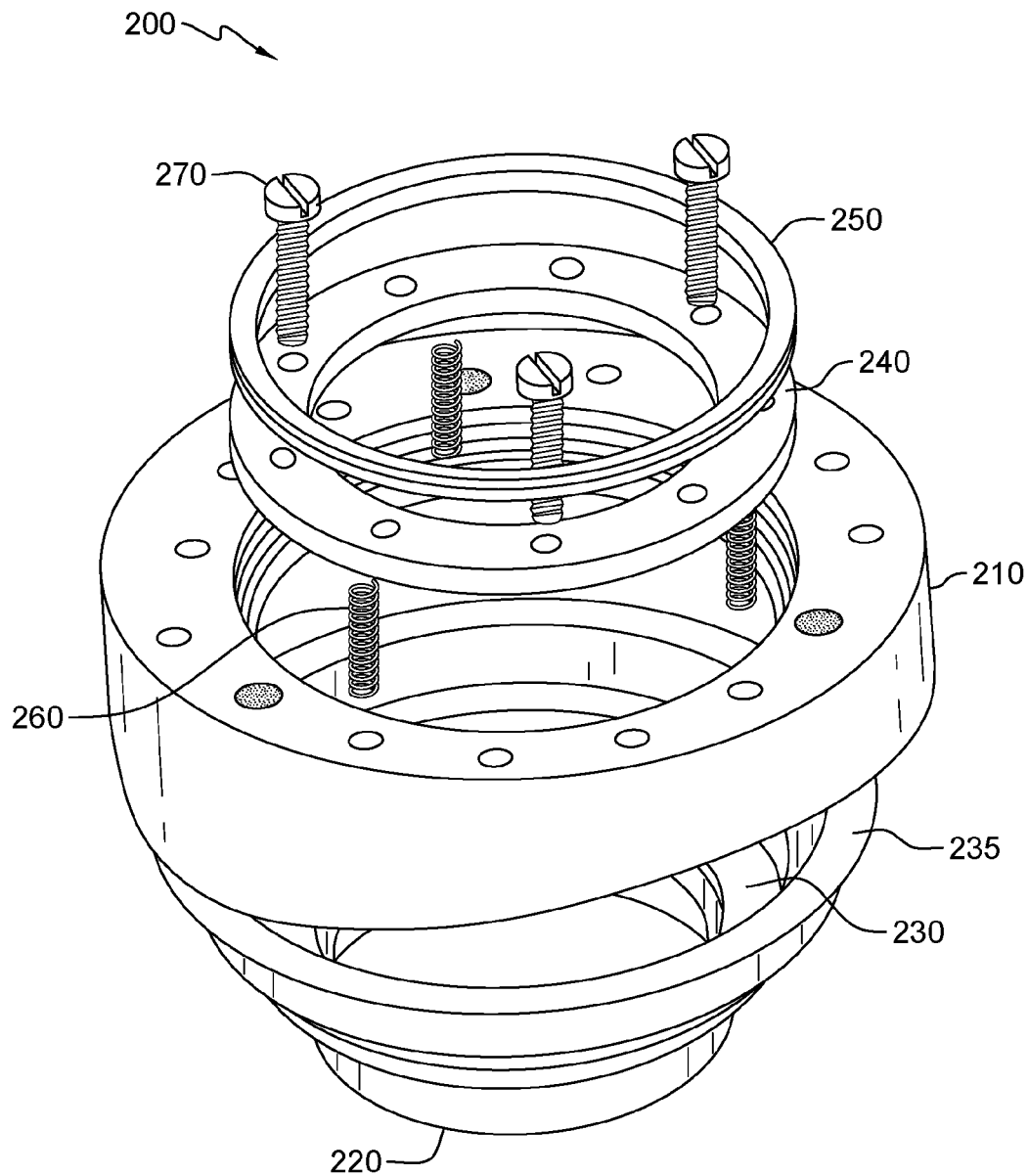
FIG. 2 shows an example of a partially assembled implant including a protective covering and springs for a resistance member in accordance with aspects of the present disclosure.
Figure 3:
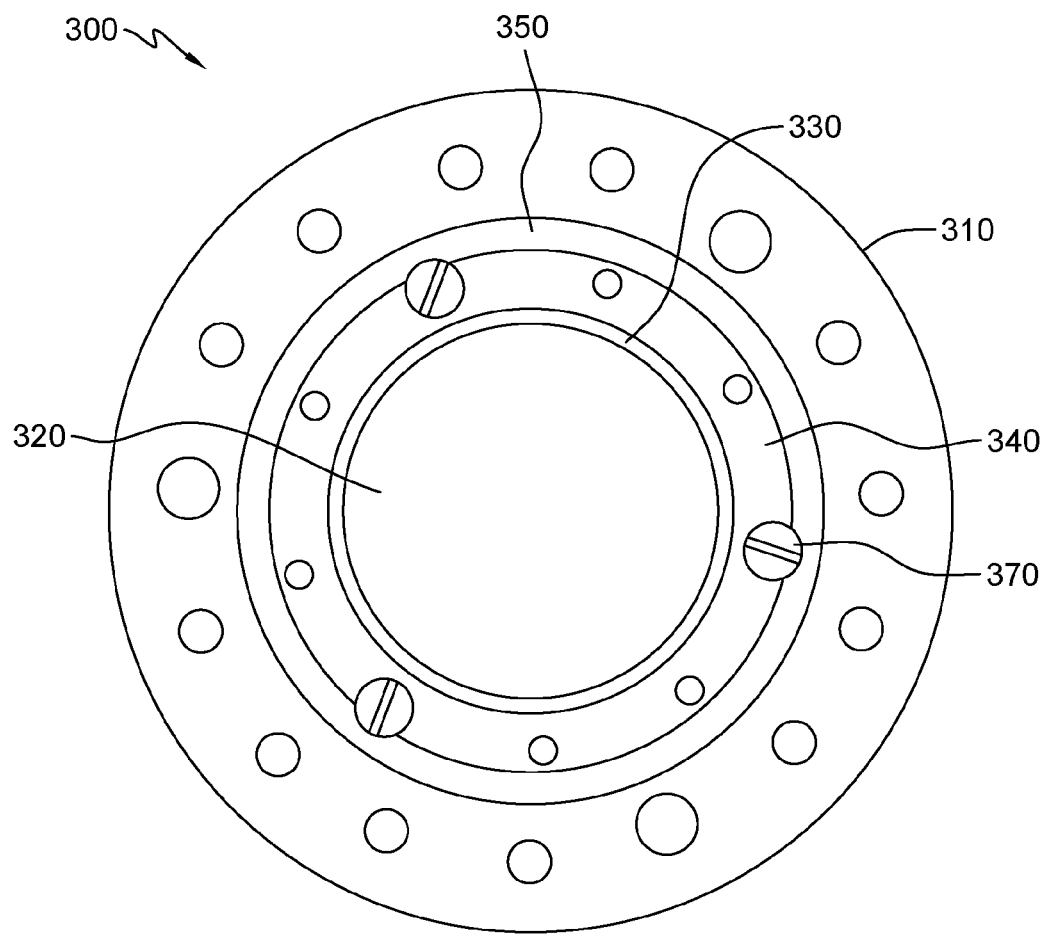
FIG. 3 shows an elevation view of an example of an implant in accordance with aspects of the present disclosure.

Another example of an implant 200 as disclosed herein is shown in FIG. 2. In this example, shown are a chamber 210, a cover slip 220, a cup 230, a protective cover 235, a setting member 240, a securing member 250, an opposing member (in this example a plurality of springs) 260, and opposing members (in this case threaded screws) 270. The example shown in FIG. 2 shows components of an implant 200 as described as they may be assembled around and within a chamber 210. Another example of an implant 300 is shown in FIG. 3. Implant 300 is shown from a perspective view above a chamber 310 with other components inserted in an opening within a chamber 310. Shown are a cover slip 320, cup 330, setting member 340, securing member 350, and opposing member 370. A resistance member (not shown) may be positioned below the setting member 340.

Such an implant may be used by affixing it to a primate's skull (e.g., with screws affixing the chamber to the skull). Visualization of the brain or other soft tissue through the cover slip may therefore be possible. It is desirable to maintain a close proximity between a cover slip and a surface of the brain for long-term use of such implant, because if the distance is too great cells may infiltrate the region between the cover slip and the brain and obscure the visibility of the brain. For example, it may be desirable to maintain a distance of less than 30 µm between a cover slip and the surface of the brain so that cells that form a biofilm, or attempt to reform meningeal tissue, may be excluded from the region therebetween.

However, some degree of flexibility of the distance between the coverslip and tissue such as brain surface, and between the cover slip and setting member, is also desirable because the brain, over time, may shift or move or get closer or farther away from the inner surface of the skull. If there is no flexibility with regard to how far the cover slip may get to or from the setting member, damaged to brain or other tissue may result. For example, if the cover slip cannot draw any closer to the skull in response to pressure exerted by the brain as the brain moves closed to the inner surface of the portion of the skull to which the chamber is attached, the cover slip may apply too much pressure on the surface of the brain, causing neural or circulatory damage. As provided herein, a resistance member permits fluctuation between the distance of the cover slip from the skull or setting member. At the same time the opposing member ensures that the cover slip remains sufficiently close to the surface of the brain to prevent biofilm formation or formation of other features that may occlude visibility. The opposing member may be adjustable such that a minimum allowable distance between a setting member and a cover slip may be modified. For example when an opposing member includes one or more screws with heads extending above, for example, the setting member, the screws may be tightened or loosened to increase or decrease, respectively, a minimum allowable distance between a setting member and a cover slip.

A microscope, camera, or other device may be inserted within the chamber to permit observation, microscopy, or filming of the tissue or body cavity, e.g. brain.

Components may be made of any suitable material, such as PEEK, and can be made to conform to a surface of the skull or other bone. An implant may be of any suitable size for visualizing any cavity or other body or organ system desired, transosseously, intraosseously, or otherwise (e.g., to visualize tissue within bone marrow).

Figure 4:
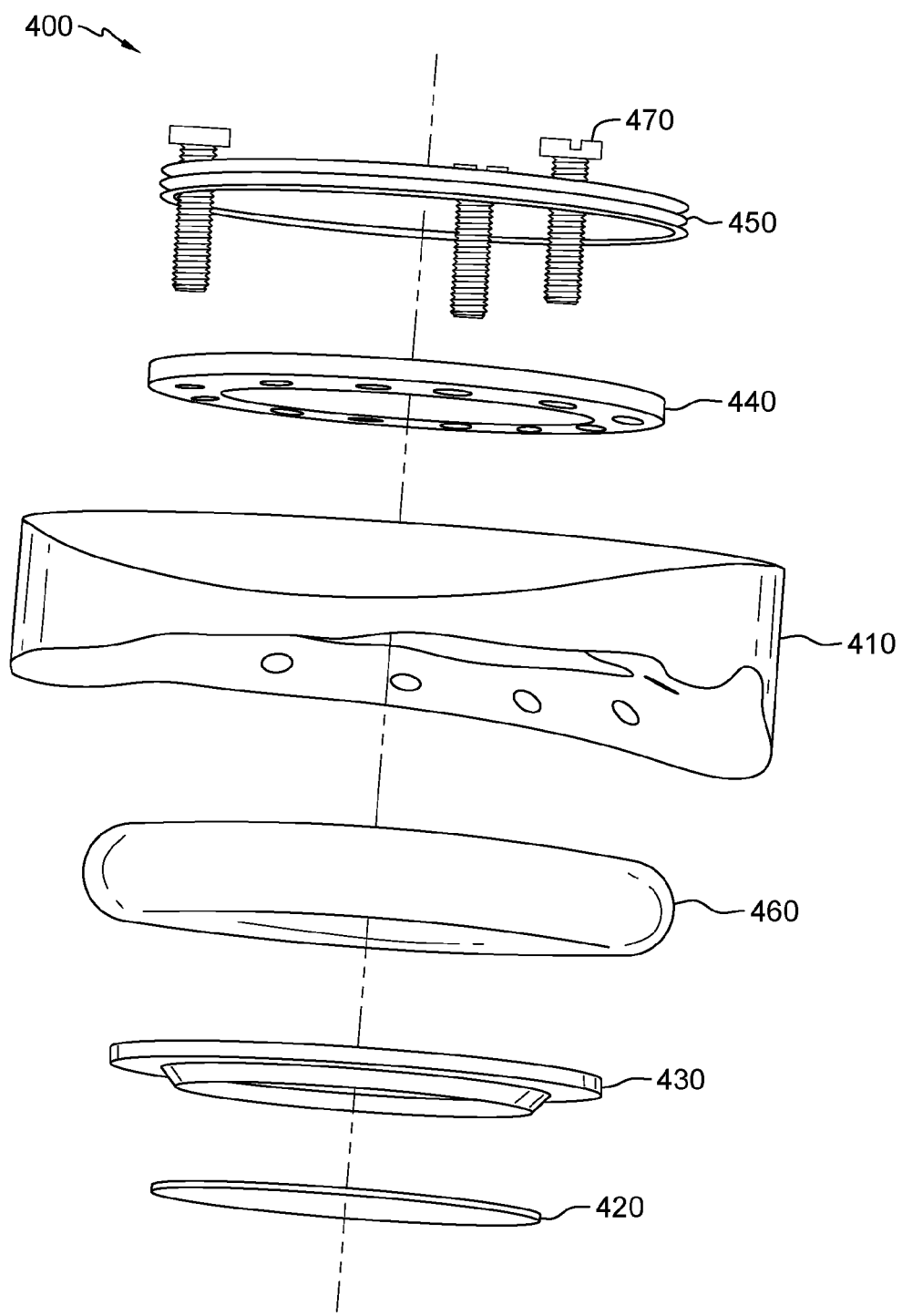
FIG. 4 shows an example of an implant with hydrogel for a resistance member in accordance with aspects of the present disclosure.

A different example of an implant 400 is shown in FIG. 4. Shown are the cover slip 420, cup 430, chamber 410, setting member 440, securing member 450, and opposing member 470. Also shown is a resistance member 460. In this example a resisting member 460 is a hydrogel, formed in a ring in this example. A hydrogel 460 may be, for example, 5% (w/v) sodium alginate crosslinked with calcium. Other percentages of sodium alginate, or other known hydrogel components, and other cross-linkers, may also be used. A hydrogel 460 may connect to an edge or lip of a cup 430 distal to a cover slip 420 and to a setting member 440 to create a sealed environment. For example, a central opening may be created by the setting member 440, resistance member 460, and cup 430 being affixed to one another, with the cover slip 420 at its bottom. It may be sealed to prevent contamination by bacteria or other undesirable substances and may be impermeable to liquids such that liquids may be disposed therein and maintained therein without leakage therefrom. An arrangement with the protective cover (not shown in FIG. 4) may be made comparable to the example shown in FIG. 1. For some types of microscopy it may be desirable to dispose fluid or oil within the cup atop the cover slip. Sealing the components together may prevent leakage of such substances out of the region and into the body cavity.

Figure 5:
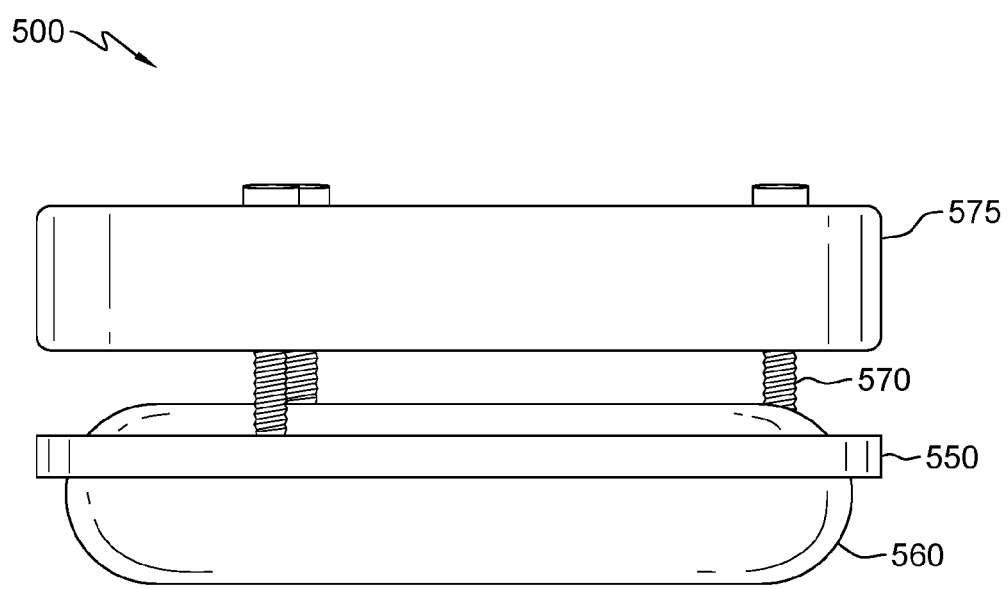
FIG. 5 shows an example of an implant with hydrogel for a resistance member implanted below a bone flap in accordance with aspects of the present disclosure.

Another example of an implant 500 in accordance with aspects of the present invention is shown in FIG. 5. According to this non-limiting example, an implant 500 may include a securing member 550 disposed on a resisting member 560 (shown in this example as a hydrogel). An implant 500 may be implanted under a bone flap 575. For example, a portion of bone such as skull may be removed, a resisting member 560 and securing member 550 positioned on the soft tissue under the bone such as on the surface of the brain, then the resected bone flap replaced and affixed to the skull. In such an example, a resisting member 560 and securing member 550 may be indwelling between the bone flap 575 and, in an example, brain. Opposing members 570 may maintain a minimum allowable distance between a bone flap 575 and a securing member 550 or cup (not shown) or cover slip (not shown) positioned within a central opening through the resisting member 560 and/or securing member 550.

Figure 6:
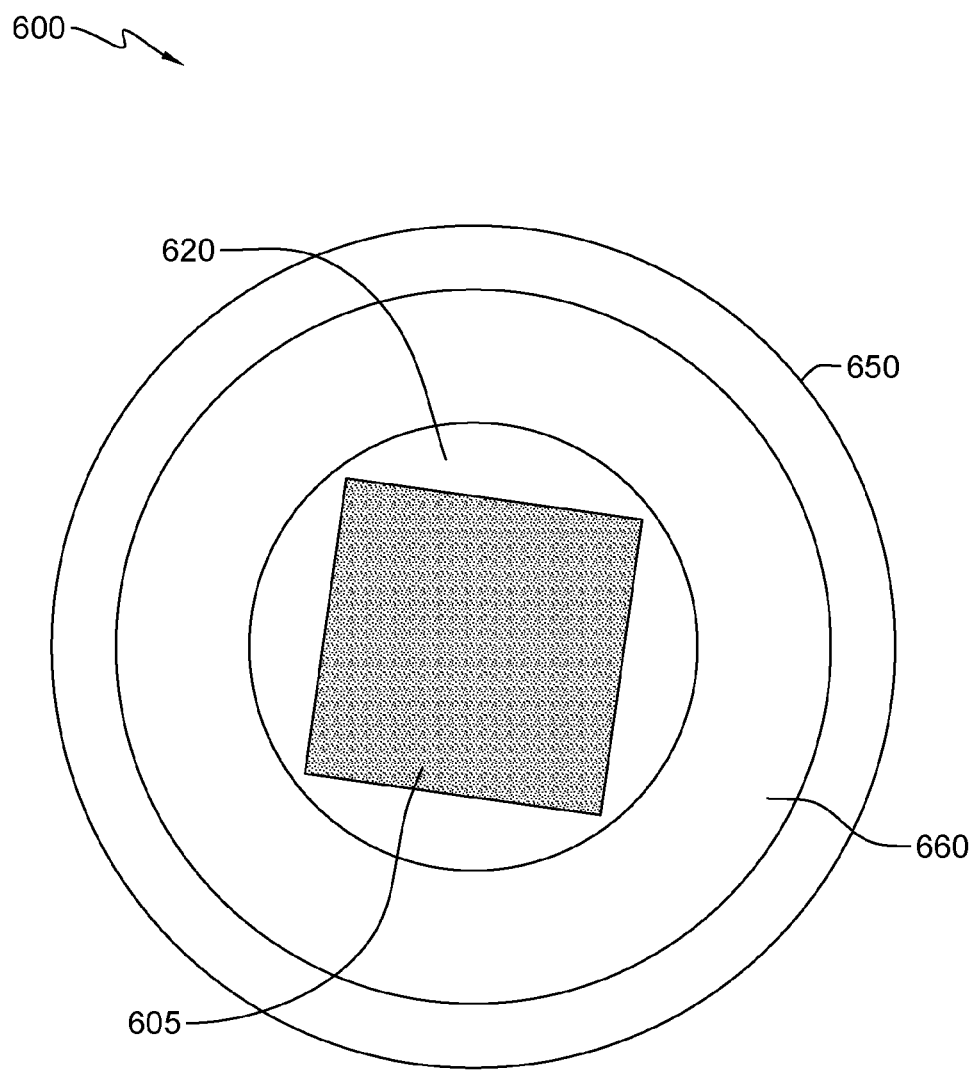
FIG. 6 shows an example of an implant with a visualizing device in accordance with aspects of the present disclosure.

Another perspective of an implant 600 is depicted as a non-limiting example in FIG. 6. The implant 600 depicted in FIG. 6 shares similarities with the implant 500 as depicted in FIG. 5. FIG. 6 is a view of an implant 600 from above, i.e. from the perspective of above the skull looking down at the brain, with the implant 600 between, such as after resection of a bone flap and after positioning an implant 600 on the underlying soft tissue such as brain before, optionally, resetting and reattaching the bone flap above the implant 600. Depicted are a resisting member 660, securing member 650 and cover slip 620, the cover slip 620 positioned in an opening within a resisting member 660 (here a hydrogel) and securing member 650.

On a cover slip 620 is depicted a visualizing device 605. A visualizing device 605 may be a camera or other device for photographing or videoing tissue. A visualizing device 605 may be wired for direct electrical connection to a computer or processor or server for sending and receiving electrical signals therebetween to control operation of the visualization device 605 and for the visualization device 605 to send digitized information representing the images observed of tissue such as brain. In another example, a visualizing device 605 may be wireless such that it can send and/or receive such information over a wireless LAN or other network. A visualization device 605 may include a battery or be powered through a wire that provides electrical power thereto. In an example, a wireless, battery-powered visualization device may be indwelling, with other components of an implant 600 as depicted in FIGS. 5 and 6, such as a securing member 650 and a resisting member 660 and a cover slip 620.

Figure 7:
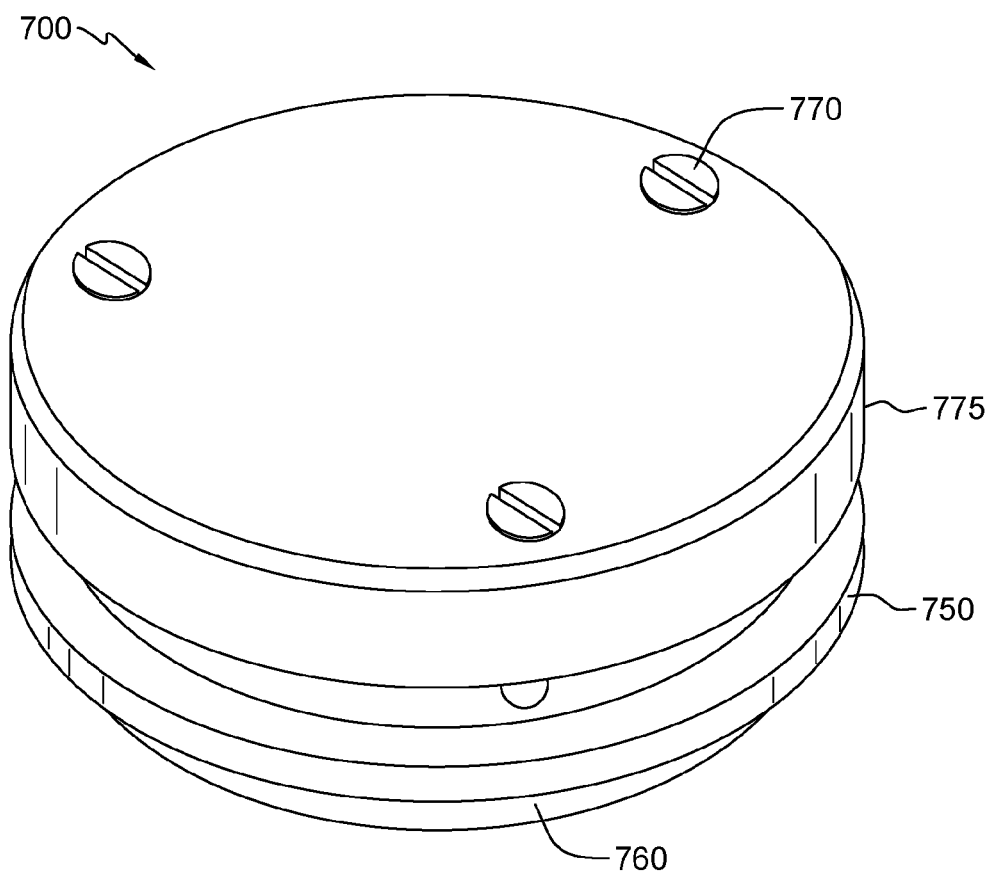
FIG. 7 shows an example of an implant implanted below a bone flap in accordance with aspects of the present disclosure.

In an example, as a resisting member expands or contract in response to loss of pressure or increased pressure, respectively, exerted on a cover slip 620 by brain or other tissue, a cover slip 620 may move away from or towards, respectively, the skull or opening therein through which it was deposited on the brain or bone flap secured thereabove. Such a configuration where a wireless visualization device 605 is used may permit observation of soft tissue wirelessly in a freely moving subject or otherwise untethered subject such as if electronic control and data information may be sent to and from the visualization device 605. A similar implant 700 is depicted in FIG. 7. Shown in FIG. 7 is a resisting member 760, securing member 750, bone flap 775, and opposing member 770 shown as a plurality of bone screws through the bone flap. When implant 700 is implants in a cranial cavity, for example, of a subject, securing member 750 and resisting member 760 (as well as visualizing device, cover slip, and, optionally, a cup and/or a protective cover, not shown) may be indwelling within the cranial cavity below the re-secured bone flap. In an example, if the visualization device is not wireless, wires or junctions for connecting wires may protrude from the skull such as through the bone flap for connecting the visualization device to a computer or microprocessor or server or power source or any combination of two or more thereof.

Figure 8:
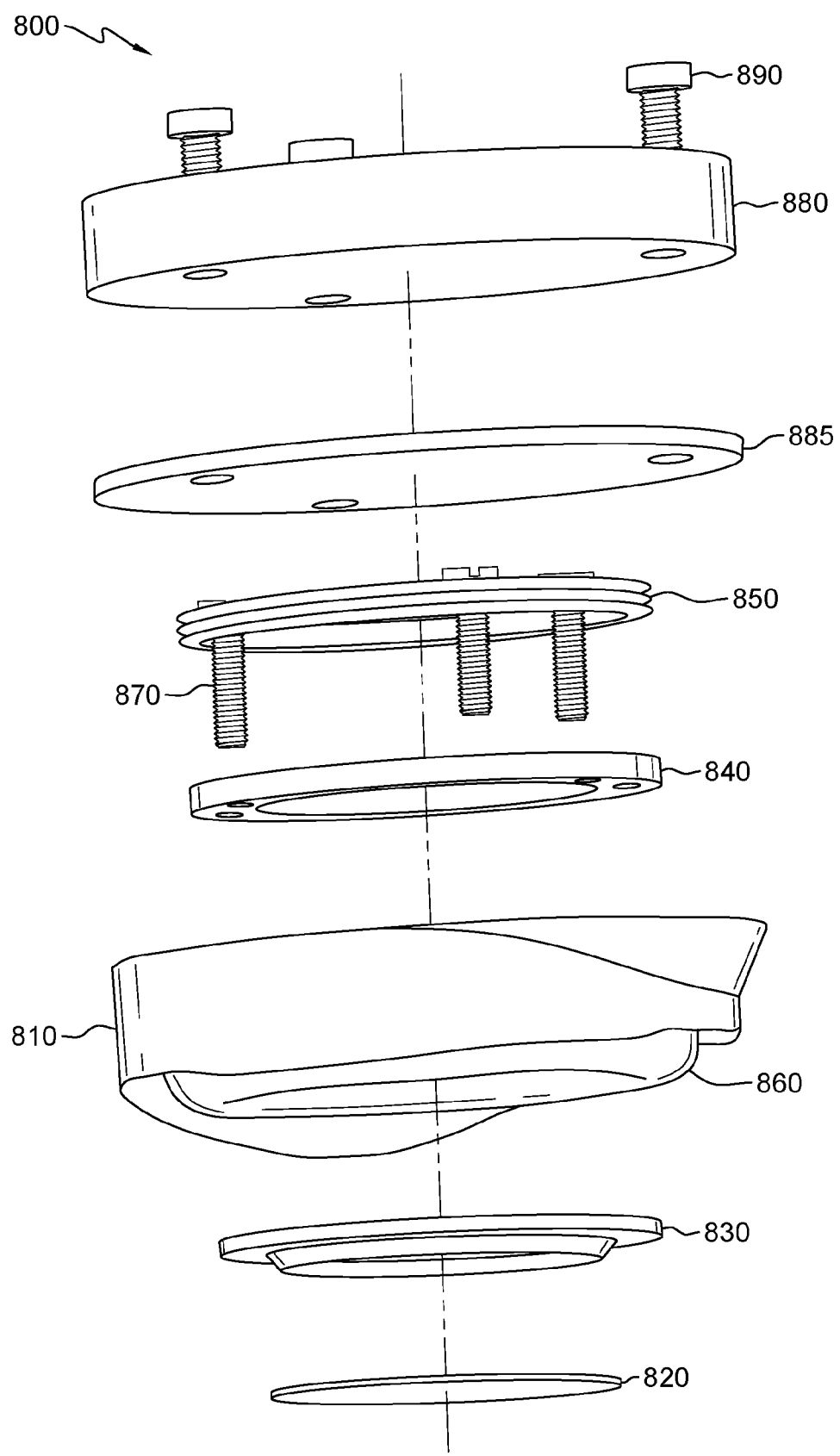
FIG. 8 shows an example of an implant with hydrogel for a resistance member and a cap in accordance with aspects of the present disclosure.

Another non-limiting example of an implant 800 in accordance with aspects of the present disclosure is depicted in FIG. 8. Shown are a cover slip 820, cup 830, resisting member 860 (a hydrogel in this example), chamber 810, setting member 840, securing member 850, and opposing member 870, substantially in accordance with description presented hereinabove. In an example, after implantation of the foregoing but between sessions during which tissue such as brain is being observed, in may be desirable to close and secure the cranial, or other, cavity. In the example depicted in FIG. 8, included are a cap 880, gasket 885, and screws 890. A cap may be placeable and reversibly securable by threading screws 890 through holes in the cap 880 and into receiving holes in for example the chamber 810 which itself is affixed to the skull. A gasket 885 below the cap 880 may be included as described above for improving the seal between the cap 880 and the chamber 810.

Figure 9:
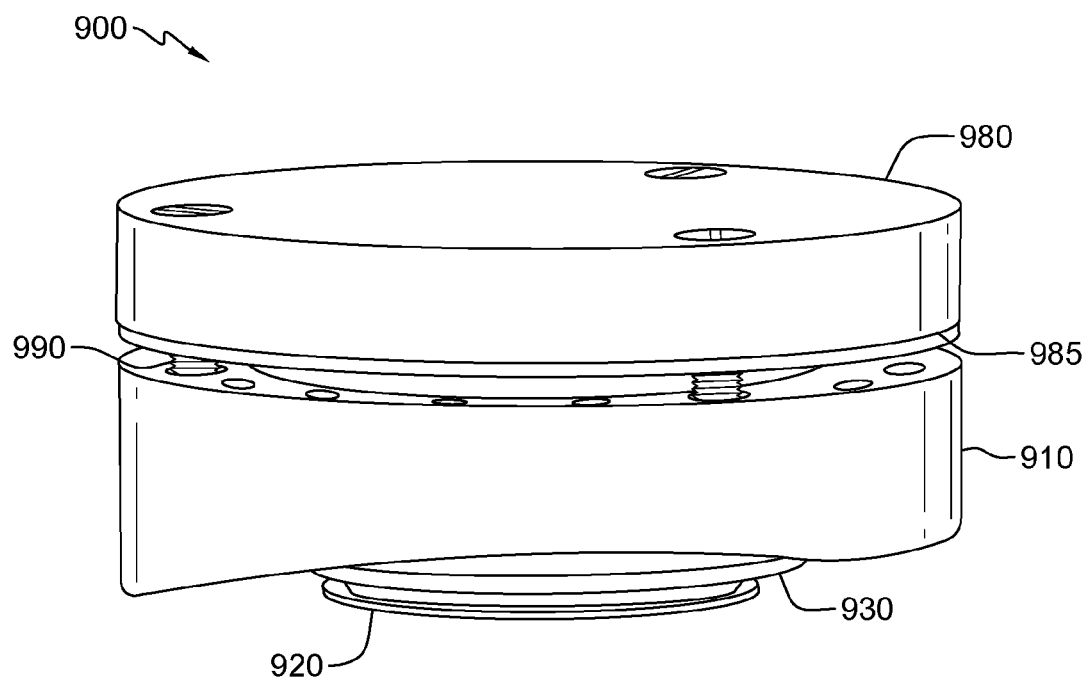
FIG. 9 shows an example of an assemled implant with a cap in accordance with aspects of the present disclosure.

A similar, non-limiting example of an implant 900 in accordance with aspects of the present disclosure is depicted in FIG. 9. Shown are a cover slip 920, cup 930, chamber 910, gasket 985, cap 980, and bone screws 990, with the cap 980 secured to the chamber 910.

In some examples, a resisting member may be configures to release drugs or other bioactive compounds. For example a hydrogel resisting member may be injected or formulated to contain a given level or concentration of drug or other substance whose release into tissue such as brain may be desirable. In some examples, such drug or other substances may be periodically loaded into a hydrogel or other resisting mere such as by being injected therein for controlled or other long-term, or in other examples immediate, release into tissue such as brain.

Long-term exposure to pressure to tissue may induce ischemia or other damage. Thus it may be desirable to have an implant as disclosed herein that permits pressure on a cover slip by tissue such as the brain to displace the cover slip rather than permit prolonged, damaging force pressure exerted on the tissue by the cover slip. A resisting member may permit such give. At the same time, it may be desirable that a cover slip remain sufficiently close to tissue such as the surface of the brain to prevent formation of other tissue or biofilm to occlude visibility. An opposing member as disclosed herein may permit keeping such proximity.

EXAMPLES

The following examples are intended to illustrate particular embodiments of the present disclosure, but are by no means intended to limit the scope thereof.

Although preferred embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

Implants in accordance with the present disclosure have been used in two macaques (NHP). An implant lasted approximately five months in the first NHP before he expired due to an unrelated issue. Another second implant had been in use for over six weeks and continued to be in use as of the time of filing the present application. The bottom implants were cut to match the corresponding bone surface covered. Any gaps remaining between the implant and bone were filled with METABOND® to ensure a tight fit. Hydrogel and silicone materials were used as resistance members. Both implants were machined out of PEEK plastic and titanium parts, which are interchangeable. PEEK is known for its radiolucent properties, strength, and ability to be sterilized. Cortical area beneath the implant was transfected with different fluorescent proteins. The implants allowed for impressive imaging using 2-photon microscopy and after analysis revealed successful transfection and demonstrated that dural and pial regrowth did not occlude observability through a cover slip of an implant.

Following are non-limiting examples of dimensions of components of an implant as disclosed. Annular cup, 27.1 mm outer diameter, 19.66 mm inner diameter, 2 mm thickness. Annular setting member, 29.14 outer diameter, 21.34 inner diameter, thickness 1.5 mm. Annular securing member, inner diameter 26.82 mm, threaded circumference 30×0.75 mm, thickness 1.5 mm. Annular chamber 28.08 mm inner diameter, 53.42 mm outer diameter, thickness variable depending on contouring of underlying bone but minimum 4.5 mm. Circular cap diameter 63.42 mm thickness 4 mm. As would be well understood by skilled artisans these are but single, non-limiting examples and components of an implant may be varied in size according to specific purposes and needs.

Those having ordinary skill in the relevant field would appreciate that any number of permutations of combinations of different components of an implant disclosed herein would fall within the present disclosure. Not all implants must include all components as described, and different combinations or sub-combinations of components are specifically included within this disclosure. An implant may include any two or more of the components for an implant disclosed herein while still being included within this disclosure and all such examples are contemplated and included herein.

What is claimed is:

1. An implant, comprising
a chamber having an interior radius wherein the interior radius has a flange,
a cover slip, a cup, a setting member, a securing member, a resistance member, and an opposing member,
wherein the cover slip, cup, resistance member, and setting member are attached to one another and the cup, resistance member, and setting member are on a same side of the cover slip as one another,
the setting member sets on the flange and the securing member secures the setting member to the flange,
the resistance member comprises a flexibility and a longitudinal axis with a length wherein the flexibility permits modification of the length,
the opposing member sets a minimum length of the longitudinal axis, and
the cover slip comprises a window for observing tissue.

2. The implant of claim 1, wherein the resistance member comprises a hydrogel, one or more springs, silicone, or rubber.

3. The implant of claim 2, wherein the resistance member comprises one or more springs and the implant further comprises a protective cover between the one or more springs and the cup.

4. The implant of claim 3 wherein the opposing member comprises one or more screws extending from the setting member and abutting the cup or the protective cover.

5. The implant of claim 1 wherein the resistance member comprises a silicone and the silicone comprises a weight ratio of hybrid vinyl-functional siloxane polymer mix (P) to platinum catalyst (C) to silicone-based oil (O) and the weight ratio of P:C:O is 2:10:30.

6. The implant of claim 1 wherein a Young's Modulus of the resistance member is between 0.5-1.0 kPa.

7. The implant of claim 1 further comprising a cap.

8. The implant of claim 1 wherein the opposing member comprises one or more screws extending from the setting member and abutting the cup.

9. The implant of claim 1 wherein an outer radius of the setting member comprises setting member threads and the inner radius comprises chamber threads and the setting member threads mate with the chamber threads.

10. The implant of claim 1 wherein the inner radius comprises slots and an outer radius of the setting member comprises tabs and the setting member tabs mate with the slots.

11. A method of using the implant of claim 1 comprising affixing the chamber to a skull of a mammal.

12. The method of claim 11 wherein the mammal is a primate.

13. The method of claim 11 wherein the chamber is affixed to the skull for at least 6 months.

14. The method of claim 11 wherein the chamber is affixed to the skull for at least 12 months.

15. An implant, comprising
a cover slip, a cup, a setting member, a resistance member, and an opposing member, wherein
the cup, resistance member, and setting member are on a same side of the cover slip as one another,
the resistance member comprises a flexibility and a longitudinal axis with a length and the opposing member sets a minimum length of the longitudinal axis, and
the cover slip comprises a window for observing tissue.

16. The implant of claim 15, wherein the resistance member comprises a hydrogel, one or more springs, silicone, or rubber.

17. The implant of claim 15, wherein the resistance member is a hydrogel.

18. The implant of claim 15 wherein the resistance member is one or more springs.

19. The implant of claim 15, wherein the resistance member is silicone.

20. The implant of claim 15 wherein the opposing member comprises one or more screw having a head and the one or more screws are configured to extend between an inner surface of a bone and an outer surface of the setting member.

21. The implant of claim 20 wherein the setting member is configured to be located between the one or more head and the bone.

22. The implant of claim 20 wherein the one or more head and the setting member are configured to be located on opposite sides of the bone.

23. A method of using the implant of claim 15 comprising implanting the implant in a mammal between a brain and a skull of the mammal.

24. The method of claim 23 wherein the mammal is a primate.

25. The method of claim 23 wherein the implant is implanted for at least 6 months.

26. The method of claim 23 wherein the implant is implanted for at least 12 months.

* * * * *